US00PP24529P3

(12) United States Plant Patent
Blazkova

(10) Patent No.: US PP24,529 P3
(45) Date of Patent: Jun. 10, 2014

(54) VARIETY OF CHERRY TREE NAMED 'ARAMAT'

(50) Latin Name: *Prunus avium*
Varietal Denomination: Aramat

(75) Inventor: Jitka Blazkova, Horice (CZ)

(73) Assignee: Research and Breeding Institute of Pomology Holovousy, Ltd., Horice (CZ)

( * ) Notice: Subject to any disclaimer, the term of this patent is extended or adjusted under 35 U.S.C. 154(b) by 107 days.

(21) Appl. No.: 13/135,803

(22) Filed: Jul. 14, 2011

(65) Prior Publication Data
US 2013/0019354 P1 Jan. 17, 2013

(51) Int. Cl.
*A01H 5/00* (2006.01)

(52) U.S. Cl.
USPC ..... Plt./181

(58) Field of Classification Search
USPC ..... Plt./181
See application file for complete search history.

*Primary Examiner* — Kent L Bell
(74) *Attorney, Agent, or Firm* — The Webb Law Firm

(57) ABSTRACT

A new and distinct cherry tree that produces sweet cherry fruits in high quantities.

3 Drawing Sheets

Botanical classification: *Prunus avium.*
Varietal denomination: 'Aramat'.

BACKGROUND OF THE INVENTION

The present invention comprises a new and distinct cultivar of *Prunus avium* known by the varietal name 'Aramat'. The new variety was discovered in Holovousy, the Czech Republic in 1994. The new variety is the result of planned breeding between 'Krupnoplodnaja' (*Prunus avium*) (female parent, unpatented) and 'Van' (*Prunus avium*) (male parent, unpatented). The new variety is similar to its parental varieties in fruit skin color, fruit firmness, and flesh color. The new variety differs from its parental varieties in fruit quality, fruit shape, and fruit pedicel length. When compared to unpatented variety 'Kordia' (*Prunus avium*), the new variety is similar in fruit time of ripening and flesh firmness, but differs in fruit size and shape, as well as susceptibility to cracking. The purpose of breeding the new variety was to provide cherries with improved fruit quality. The new variety was first asexually reproduced via grafting. The new variety has been trial and field tested and has been found to retain its distinctive characteristics and remain true to type through successive propagations. The following characteristics distinguish the new variety from other varieties known to the breeder:

1. Fruit size;
2. Flesh firmness; and
3. Sweet tasting fruits.

DESCRIPTION OF THE DRAWINGS

The accompanying photographic drawings illustrate the new variety, with the color being as nearly true as is possible with color illustrations of this type.

DETAILED BOTANICAL DESCRIPTION

Figure 1:
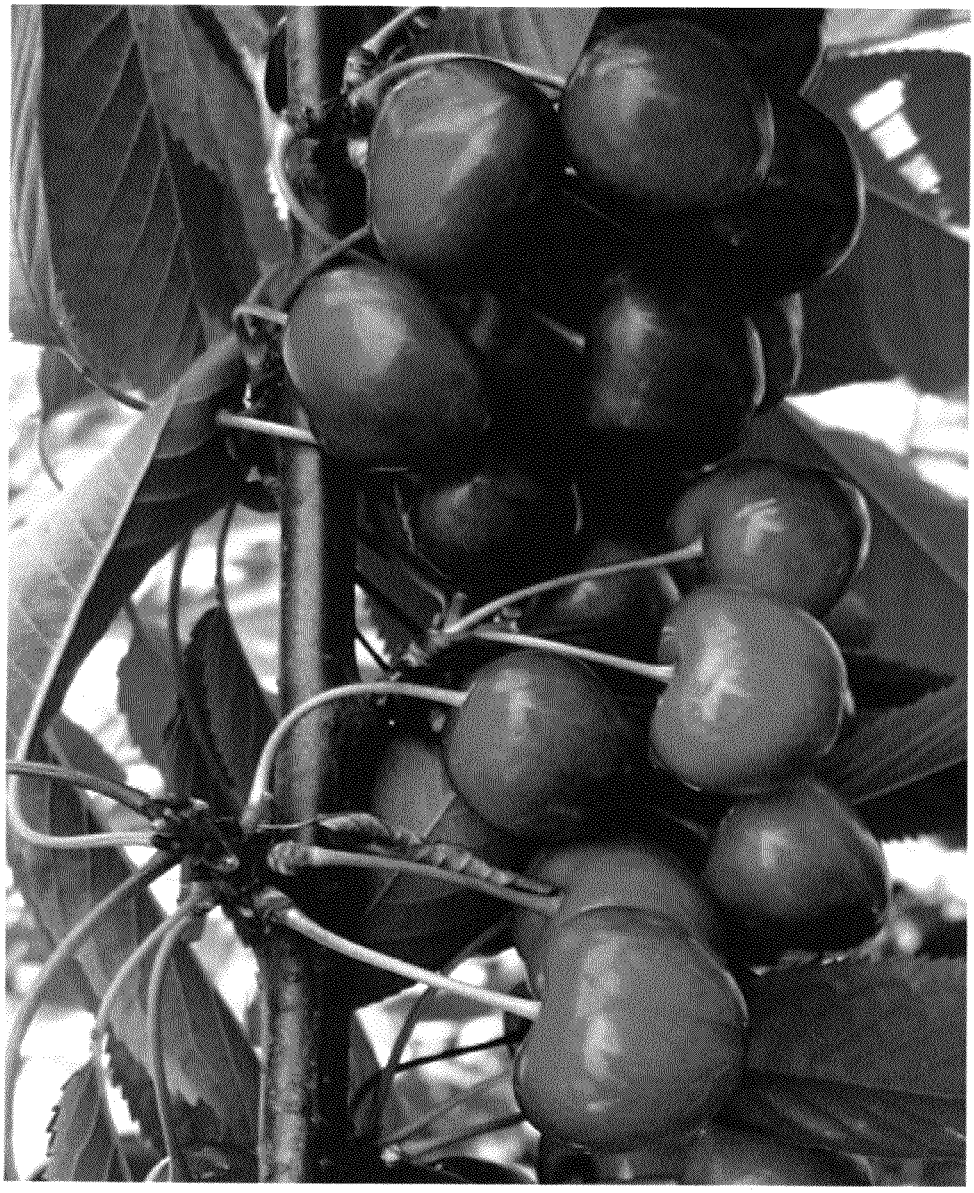
FIG. 1 is a close-up photograph of the fruit of 'Aramat'.
Figure 2:
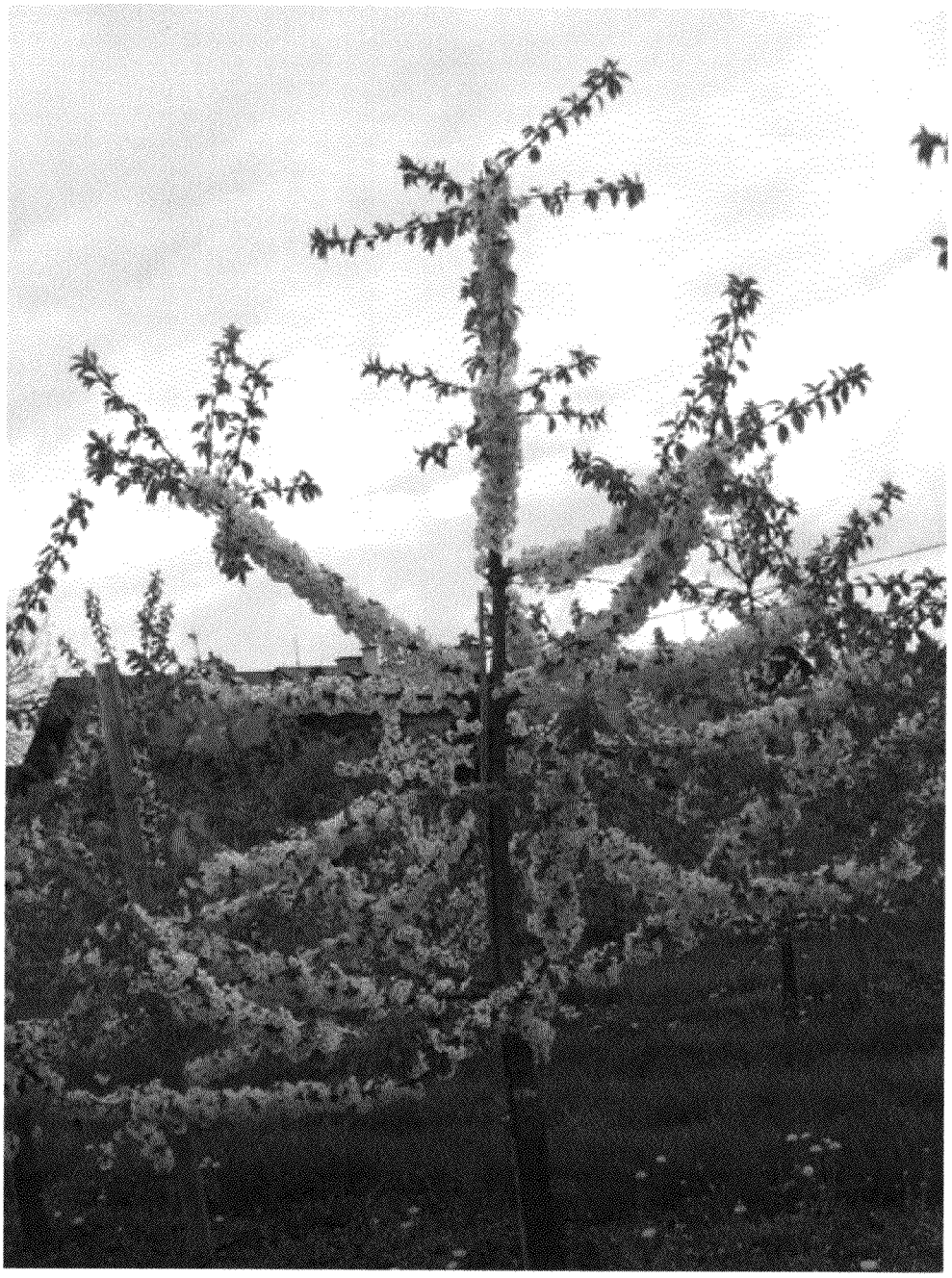
FIG. 2 is a photograph of an entire tree of the new variety.
Figure 3:
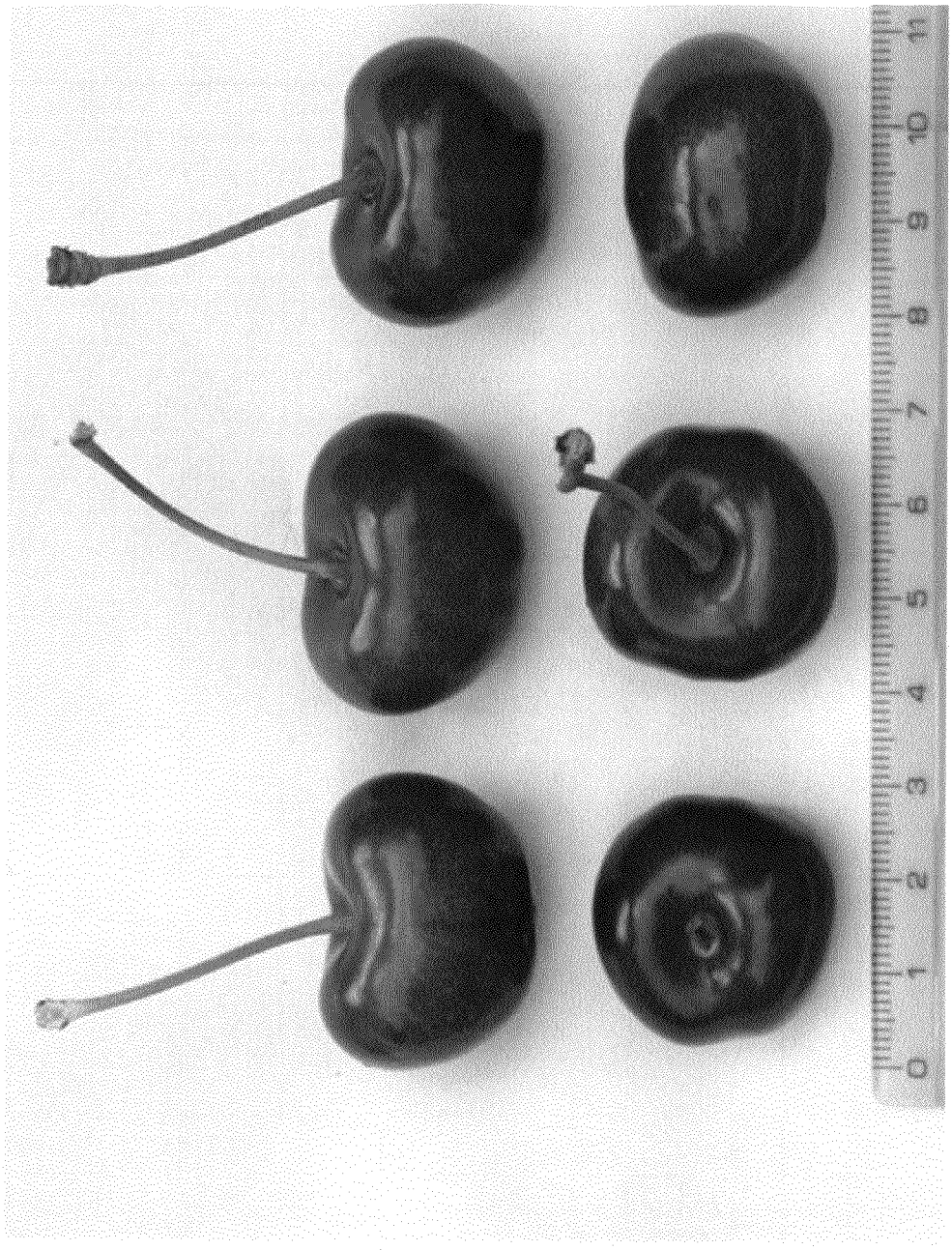
FIG. 3 is a photograph showing measurements of the fruit of 'Aramat.'

The following detailed description sets forth the characteristics of the new Cultivar. The data which defines these characteristics were collected by asexual reproductions via grafting carried out in Holovousy, the Czech Republic. The new variety was grown in an orchard under standard growing conditions outdoors in the Czech Republic. The color readings were taken in natural daylight, and the plant was 6 years old when described. Color references are primarily to The 1995 R.H.S. Colour Chart of The Royal Horticultural Society of London.

Tree
Height: 3.0 m.
Spread: 4.5-6.0 m.
Vigor: Medium.
Density: Medium.
Form: Spreading.
Bearing: High.
Growth type: Average; similar to 'Bing', 'Van' and 'Rainier' cherry trees.
Rootstock compatibility: Good with cherry rootstocks 'Colt' and 'Gisela 5'.
Trunk:
- *Diameter.*—88 mm.
- *Bark color.*—200A.
- *Surface texture.*—Rough.
- *Lenticels.*—Length: 10.0-15.0 mm. Width: 1.0-2.0 mm. Color: 175D. Density: High.

Branches:
- *Diameter.*—At 2 years: 15.8 mm. At 3 years: 17.5 mm. At 4 years: 23.0 mm. At 5 years: 30.0 mm.
- *Surface texture.*—Smooth.
- *Color.*—200B.
- *Form.*—Slightly drooping.
- *Average angle.*—60°.
- *Bud arrangement.*—3 to 5 per side, in clusters.
- *Lenticels.*—Length: 2.0 mm. on 2 year old trees. Shape: Long and elliptical. Diameter: Approximately 0.5 mm on average. Color: 175D. Density: Intermediate to high; approximately 5 per 1.0 $cm^2$. Shape: Small and rounded early in growth; on older bark, the lenticels are elongated and numerous.

Leaves:

*Length.*—110.5 mm.

*Width.*—52.0 mm.

*Form.*—Oval.

*Texture.*—Smooth.

*Thickness.*—Intermediate.

*Base.*—Long and cuneate.

*Apex.*—Long and pointed.

*Margin.*—Serrate and obtuse.

*Pubescence.*—Upper surface: None. Lower surface: None.

*Color.*—Upper surface: 135C. Lower surface: 136C.

*Petiole.*—Length: 40.0 mm. Diameter: 1.5 mm. Color: Light red color (approximately 182D) present at the base of the petiole.

*Vein color.*—59B.

Flower buds:

*Pedicel.*—Length: 1.5 mm. Diameter: 6.8 mm. Color: 200A.

*Bud.*—Length: 15.0 mm. Width: 3.2 mm. Color: 166A. Apex: Pointed. Margin: Rounded.

Flowers:

*Average diameter.*—22.0 mm.

*Blooming timing.*—Medium early to early; average date of first bloom is April 12th.

*Blooming period.*—6-14 days.

*Number of flowers per raceme.*—3-5.

*Fragrance.*—None present.

*Petals.*—Number: 5. Length: 16.0 mm. Width: 15.0 mm. Shape: Oblong. Margin: Entire. Apex: Rounded. Base: Cuneate.

*Color.*—Upper surface: 155B. Lower surface: 155B.

*Sepals.*—Average number: 5. Shape: Elongated and tapered. Length: 7.0 mm. Diameter: 3.0 mm. Apex: Acute. Margin: Entire. Color: Inner surface: 138A. Outer surface: 138A with 60A at edge.

*Pollen.*—Color: 17A. Amount (generally): Plentiful.

*Reproductive organs.*—Anther superior to pistal with 26 anthers on average.

Fruit (described at full maturity):

*Picking.*—Average time is medium to late season in Holovousy, the Czech Republic; around the 5th and 6th cherry week.

*Size.*—Weight: 10 grams. Diameter: 30.2 mm. Length: 26.2 mm.

*Shape.*—Apex: Rounded. Base: Truncate.

*Skin.*—Thickness: Medium. Texture: Intermediately fibrous. Tendency to crack: Intermediate. Color: 46A.

*Flesh.*—Aroma: Strong. Color: 47D. Texture: Intermediately fibrous and firm. Eating quality: Excellent and sweet taste.

*Seeds.*—Number per fruit: 1. Length: 11.2 mm. Breadth: 10.6 mm. Form: Spherical. Color: 159A.

*Stem.*—Color: 138B. Length: 40.0-42.0 mm. Width: 1.2 mm. Stem cavity: Depth: Average of 2.0 mm. Diameter: Average of 10.0 mm. Yield: Heavy, similar to 'Rainier'.

Keeping quality: Good.

Shipping quality: Good.

Tree winter hardiness: Medium.

Bud winter hardiness: Good.

Drought tolerance: Good.

Disease/pest resistance or susceptibility: Nothing unusual observed.

I claim:

1. A new and distinct variety of cherry tree, as is herein illustrated and described.

* * * * *